United States Patent [19]

Schwartz et al.

[11] Patent Number: 5,162,285
[45] Date of Patent: Nov. 10, 1992

[54] PREPARING CATALYST FOR THE CATALYTIC OXIDATION OF OLEFINS TO CARBONYL COMPOUNDS

[75] Inventors: Jeffrey Schwartz, Princeton; H. Eric Fischer, E. Windsor; Jeffrey W. McMillan, Plainsboro, all of N.J.

[73] Assignee: Princeton University, Princeton, N.J.

[21] Appl. No.: 867,730

[22] Filed: Apr. 10, 1992

Related U.S. Application Data

[62] Division of Ser. No. 619,359, Nov. 28, 1990, Pat. No. 5,126,490.

[51] Int. Cl.$^5$ .......................... B01J 23/46; B01J 37/00
[52] U.S. Cl. ...................................... 502/332; 502/74; 502/84; 502/261
[58] Field of Search ................... 502/74, 84, 261, 332, 502/350

[56] References Cited

U.S. PATENT DOCUMENTS

| | | | |
|---|---|---|---|
| 2,747,970 | 5/1956 | Rosenblatt | 502/332 |
| 3,998,881 | 12/1976 | Butte, Jr. et al. | 502/332 |
| 4,383,940 | 5/1983 | Murtha et al. | 502/261 |
| 4,444,898 | 4/1984 | Schwartz et al. | 502/74 |
| 4,456,694 | 6/1984 | Blaskie et al. | 502/261 |

FOREIGN PATENT DOCUMENTS

| | | | |
|---|---|---|---|
| 11146 | 5/1980 | European Pat. Off. | 502/332 |

*Primary Examiner*—Carl F. Dees

[57] ABSTRACT

A process is disclosed for the catalytic oxydation of olefins to carbonyl compounds with molecular oxygen at elevated temperatures in the presence of rhodium oxide on a support. The process is applicable to a broad variety of olefins and is not limited to special olefins and forms especially ketones in a high selectivity.

6 Claims, No Drawings

PREPARING CATALYST FOR THE CATALYTIC OXIDATION OF OLEFINS TO CARBONYL COMPOUNDS

This is a divisional of copending application Ser. No. 07/619,359 filed on Nov. 28, 1990, now U.S. Pat. No. 5,126,490.

FIELD OF THE INVENTION

The present invention relates to the catalytic oxidation of olefins, more specifically it is directed to the production of carbonyl compounds by the oxidation of olefins catalysed by a rhodium oxide on a support.

BACKGROUND OF THE INVENTION

Catalytic oxidation of olefins to carbonyl compounds is well known in the art.

In U.S. Pat. No. 560,803 a process is disclosed for preparing ketones by oxidation of olefins with a rhenium catalyst. However, some isoolefins are disclosed to be unreactive in forming the desired ketones using this catalyst.

In U.S. Pat. No. 3,632,833 a process is disclosed for the oxidation of propylene in the presence of rhodium metal. The product was disclosed to be mostly acrolein with minor amounts of acetone, acetic acid, propionic acid and acrylic acid.

In German OS 27 44207 a process is disclosed for the production of an oxidized product by the catalytic oxidation of an organic compound with a dioxide. The catalyst is a Rh(I) -complex and the reaction medium is a special phosphorous compound in a liquid state.

The object of the present invention is to provide a process for producing a carbonyl compound by catalytic oxidation of an olefin which is easy to conduct and which is applicable to a broad variety of olefins. Another object is to avoid the formation of undesired by-products. A further object is to provide a process for the production of rhodium catalysts.

SUMMARY OF THE INVENTION

The objects of the present invention are achieved by the present process for producing a carbonyl compound by catalytic oxidation of an olefin, according to which an olefin is contacted with molecular oxygen in a reaction zone at elevated temperature in the presence of a catalyst which is a rhodium oxide on a support.

DETAILED DESCRIPTION OF THE INVENTION

The catalyst of the present invention is a rhodium oxide on a support including (support)-rhodium-oxygen complexes, especially (support)-Rh ($O_2$) and the ozone complex (support)-Rh ($O_3$).

Suitable supports include alumina, gamma-alumina, silica, silica-alumina, zeolites, titanium dioxide, pumice, activated earths, kieselgur, clays and the like. Preferred supports are alumina and zeolites; most preferred is gamma-alumina. The supports are characterized by a specific surface area of at least about 10 square meters per gram, and more preferably from about 25 to about 200 square meters per gram (BET method).

There are two methods for the preparation of the catalyst, the organometallic method and the impregnation method.

The organometallic method is known and described in U.S. Pat. No. 4,444,898 and in JACS 1989, 111, 7644.

In general, an organometallic rhodium compound like $Rh(allyl)_3$ is reacted with a support like gamma-alumina in an organic solvent such as toluene at room temperature over a time period of from about 24 to about 120 hours to form ($Al_2O_3$) - $Rh(allyl)_2$.

To prepare the dicarbonyl complex, carbon monoxide is contacted with the support-rhodium complex at one atm at room temperature for a time period of from about 30 minutes to about 2 hours to form ($Al_2O_3$)-$Rh(CO)_2$ after removing the solvent.

To form the dioxygen complex, oxygen is contacted with the alumina-rhodium-carbon monoxide-complex at 400 mm to 760 mm pressure at 100° to 200° C. from about 48 hours to about 40 days to give ($Al_2O_3$)-$Rh(o_2)$.

To form the alumina-rhodium-ozone-complex, the alumina-rhodium-carbon monoxide-complex or the alumina-rhodium bis allyl-complex is treated with dry ozone (1% in $O_2$) at room temperature for a time period of from about 4 to about 12 hours to give ($Al_2O_3$)-$Rh(O_3)$.

In the impregnation method, a rhodium salt like $RhCl_3.3H_2O$, $Rh(NO_3)_3 \cdot 2H_2O$, $[Rh(NH_3)_5Cl]Cl_2$ or $RhCl(CO)(PPh_3)_2$, soluble in water or organic solvents like for example alcohols is added to a slurry of a support in water or said organic solvent.

Preferred rhodium-salts are $RhCl_3.3H_2O$ and $Rh(NO_3)_3.2H_2O$, most preferred is $RhCl_3.3H_2O$. The concentration of the rhodium salt in water or said organic solvent is from about 10 mg/ml to about 500 mg/ml, preferably from about 50 mg/ml to about 150 mg/ml. The slurry contains from about 500 mg to about 10 g of the support, preferably from about 1 g to about 5 g. The mixture is stirred at room temperature for about 4 to about 24 hours and then filtered. The solid is dried at elevatated temperatures of from about 50° to about 200° C., preferably from about 100° to about 150° C. for a time period of from about 0.5 to about 3 hours and then pulverized by a mortar and pestile or in a mill to give a powder of a particle size of from about 1 to about 100 μm, preferably 5 to 50 μm.

The carbonylation of the powder followed by the treatment with $O_2$ or $O_3$ is the same as described above in the organometallic method.

The resulting catalyst has a rhodium content of from about 0.1 to about 15, preferably from about 0.1 to about 10, most preferably from about 0.5 to about 5%, by weight, based on the total weight of the supported catalyst.

The supported catalyst may be used in any suitable form, such as granules, pellets, powder and the like.

Olefins useful in the present invention are linear alkenes of 2 to 20 carbon atoms, preferably 2 to 10 carbon atoms, branched alkenes of 4 to 20 carbon atoms, preferably 4 to 10 carbon atoms, cyclic alkenes of 4 to 20 carbon atoms, preferably 4 to 10 carbon atoms and unsubstituted or substituted arylalkenes of 8 to 20 carbon atoms, preferably 8 to 15 carbon atoms. Examples of useful linear alkenes are propylene, 1-butene, 2-butene, 1-pentene, 2-pentene, 1-hexene, 2-hexene, 3-hexene, 1-heptene, 2-heptene, 1-octene, 2-octene, 1-nonene, 2-nonene, 1-decene, 1-dodecene and 1-hexadecene. Preferred are propylene, 1-butene, 1-pentene and 1-hexene.

Examples of useful branched alkenes are 2-methyl-2-butene, 2,3- dimethyl-2-butene and 3-methyl-1-pentene. Preferred are 2-methyl- 2-butene and 2,3-dimethyl-2-butene.

Examples of useful cyclic alkenes are cyclobutene, cyclopentene, cyclohexene, cyclooctene, norbornene and 1-methyl-1-cyclohexene. Preferred are cyclopentene, cyclohexene and norbornene.

Examples of arylalkenes are styrene, p-methylstyrene, p-methoxystyrene, p-nitrostyrene, allylbenzene, propenyl benzene, 3-phenyl,-1-hexene, 4-o-tolyl-1-butene and 1,6-diphenyl-3-hexane. Preferred are styrene and p-methoxystyrene.

In the process of the present invention, an olefin is contacted with molecular oxygen in a reaction zone at elevated temperatures in the presence of one of the rhodium catalysts described above. The process can be carried out either batchwise, continuously or semi-continuously.

In a batchwise process, the reactants may be placed together with the catalyst in an autoclave under the desired reaction conditions for a time period sufficient to oxidize the olefin, generally from about 0.1 to about 10 hours, preferably from about 1 to about 5 hours. The reaction may be carried out in the gas phase or in a solvent, inert under the reaction conditions like for example benzene.

The continuous process may be carried out in the gas phase in a tube reactor with a fixed bed.

In a continuous gas-phase process, the gaseous reactants are passed through the fixed bed of the catalyst at temperatures of from about 70° to about 600° C., preferably from about 80° to about 300° C.

The space velocity of the gas in the reactor is not critical.

Optionally, water vapor up to the saturation point may be included in the gas stream. For example, in the oxidation of propene, propanal becomes a significant product in the presence of water vapor. Without water vapor, acetone is the only oxidation product.

Optionally, other inert gaseous diluents could be employed, including nitrogen or helium.

The products are collected in a cold trap and then isolated.

The products of the present invention are carbonyl compounds, such as ketones and aldehydes. Ketones are the preferred products. As mentioned above, the presence of water vapor may influence the relative amounts of ketone and aldehyde formation.

In general, the selectivity of the process of the present invention in terms of the formation of ketones from olefins is very high; typically, for most olefins, ketone formation is more than 90%. Acids are not typically formed by this process. Alcohols are not formed by this process.

The reaction rates in moles product per moles rhodium per hour (m/mRh/h) is from about 1 to about 400, preferably about 2 to about 350, most preferably about 2.5 to about 300 m/mRh/h.

The present process permits the oxidation of olefins with alkyl groups attached to the double bond at an even higher rate in relation to linear olefins, whereas these compounds are generally unreactive with other catalysts.

EXAMPLES

A. Impregnation Method

Preparation of the Catalyst

Two hundred fifty mg of $RhCl_3.3H_2O$ was added to a slurry of 2.0 g gamma-alumina in 50 ml of water. The mixture was stirred for 24 hrs and was then filtered. The mixture was dried at 150° C. for 2 hrs and was then pulverized to give a pink powder. 1 atm carbon monoxide was passed at 100° C. temperature over this pink powder at a pressure of about 1 atm for 24 minutes. The color changed to yellow and IR analysis showed broad bands at 2012 and 2095 $cm^{-1}$. Ozonolysis (1% ozone in $O_2$) of this yellow material at room temperature for 4 hours resulted in the disappearance of the IR absorption and a color change to off-shite. The rhodium content of the catalyst was 3% by weight in relation to the total weight of the supported catalyst.

EXAMPLE 1

7.1 g norbornene and 1 atm $O_2$ were passed over 100 mg of this material at 280° C. for 2 hours, yielding in a partial conversion 99 mg norbornanone (relative yield 70%) and 43 mg cyclohexene carboxaldehyde (relative yield 30%) with a turnover frequency of 160 moles total product per mole Rh per hr.

B. Organometallic Method

Preparation of the Catalyst 30 mg Rh (allyl)$_3$ was added to a slurry of 1 g gamma-alumina in 50 ml toluene under agitation at a temperature of 20° C. for a time period of 96 hours. After removing the toluene, 1 atm of carbon monoxide was passed over the resulting powder at room temperature for 12 hours, followed by a treatment of the powder with dry $O_2$ at 1 atm at 140° C. for 170 hours. The resulting catalyst showed a rhodium content of 1.1% by weight in relation to the total weight of the supported catalyst.

EXAMPLES 2 TO 10

100 mg of this (alumina)-Rh($O_2$) catalyst (5.6 moles Rh) was charged on a frit in a tube reactor. According to Example 1 the amount of the respective olefin in grams (g) listed in the table and 1 atm oxygen was passed over this frit at a temperature of 280° C. The flow of reagents was maintained over the catalyst for a time period in hours, listed in the table, and the products were collected in a cold trap (−78° C).

The products were analysed with quantitative gas chromatography.

In Example 3, the gas stream was saturated with water vapor pass ng the oxygen through water before mixing it with propylene. As a result, aside from acetone, propanal became a significant product.

The reaction rate is indicated in the table as moles product per moles rhodium per hour (m/mRh/h).

TABLE

| Example | Pre3p. method for Catalyst | Reaction time [hours] | Olefin [grams] | Product (rel. amounts where indicated) | Yield [mg] | Reaction rate [m/mRh/hr] | rel. rate |
|---|---|---|---|---|---|---|---|
| 1 | A | 4 | norbornene 7.1 | norbornanone (70%) cyclohexenecarboxaldehyde (30%) | 99 43 | 160 | 53 |
| 2 | B | 4 | propene 3.6 | acetone | 89 | 70 | 23 |
| 3 (+$H_2O$) | B | 4 | propene | acetone (94%), | 76 | 60 | 20 |

TABLE-continued

| Example | Prep. method for Catalyst | Reaction time [hours] | Olefin [grams] | Product (rel. amounts where indicated) | Yield [mg] | Reaction rate [m/mRh/hr] | rel. rate |
|---|---|---|---|---|---|---|---|
| 4 | B | 1 | 3.6 2,3-dimethyl-2-butene | propanal (6%) 2,2-dimethyl-2-butanone (93%) acetone (7%) | 5 123 6 | 280 | 93 |
| 5 | B | 2 | 2.8 norbornene | norbornanone (70%) cyclohexenecarboxaldehyde (30%) | 210 90 | 240 | 80 |
| 6 | B | 2 | 6.5 styrene | acetophenone (80%) 1-phenylacetaldehyde (20%) | 140 20 | 120 | 40 |
| 7 | B | 2.5 | 6.0 4-methylstyrene | 4-methylacetophenone (79%) 1-(4-methylphenyl)acetaldehyde (21%) | 240 60 | 160 | 46 |
| 8 | B | 2 | 5.1 4-methoxystyrene | 4-methoxyacetophenone (>95%) 1-(4-methoxyphenyl)acetaldehyde (<5%) | 380 20 | 240 | 80 |
| 9 | B | 3 | 10.5 4-nitrostyrene | 4-nitroacetophenone (>90%) 1-(4-nitrophenyl)acetaldehyde (<10%) | 106 10 | 43 | 14 |
| 10 | B | 4 | 3.2 cyclohexene 5.6 | cyclohexanone | 6 | 3 | 1 |

We claim:

1. A process for the preparation of a catalyst comprising:
   a) adding under agitation a solution of a rhodium salt in water or in an organic solvent to a support selected from the group consisting of alumina, gamma-alumina, silica, silica-alumina, titanium dioxide, zeolites, pumice, kieselgur and clays,
   b) drying the resulting mixture at elevated temperature and pulverizing to a powder
   c) contacting said powder with carbon monoxide and thereafter
   d) contacting with a gas selected from the group consisting of oxygen, ozone and mixtures thereof.

2. A process according to claim 1, wherein said rhodium salt is selected from the group consisting of Rh $Cl_3 \cdot 3H_2O$, $Rh(NO_3)_3 \cdot 2H_2O$, $Cl_2$ and Rh $Cl(CO)(PPh_3)_2$ 3. A process according to claim 1, wherein said support is gamma-alumina.

4. A process according to claim 1, wherein the temperature in step b) is from about 100° to about 300° C.

5. A process according to claim 1, wherein said gas in step d), is oxygen.

6. A process according to claim 1, wherein said gas in step d), is ozone.

* * * * *